(12) United States Patent
Landge

(10) Patent No.: US 6,706,953 B2
(45) Date of Patent: Mar. 16, 2004

(54) BRASSICA NAPUS PLANT LINE NUDB-38

(75) Inventor: Sudhakar Pandurang Landge, Chandrapur (IN)

(73) Assignee: Dhara Vegetable Oil and Food Company Limited, Vadodara (IN)

( * ) Notice: Subject to any disclaimer, the term of this patent is extended or adjusted under 35 U.S.C. 154(b) by 16 days.

(21) Appl. No.: 10/079,562

(22) Filed: Feb. 22, 2002

(65) Prior Publication Data

US 2002/0157134 A1 Oct. 24, 2002

Related U.S. Application Data

(63) Continuation-in-part of application No. 09/448,294, filed on Nov. 24, 1999, now abandoned.

(51) Int. Cl.$^7$ .............................. A01H 5/00; A01H 1/06
(52) U.S. Cl. ....................... 800/306; 800/298; 800/264; 800/270
(58) Field of Search ................................. 800/306, 298, 800/270, 266, 264

(56) References Cited

U.S. PATENT DOCUMENTS

| | | | | |
|---|---|---|---|---|
| 5,387,758 A | * | 2/1995 | Wong et al. ................ | 800/264 |
| 5,523,520 A | * | 6/1996 | Hunsperger et al. ........ | 800/206 |
| 5,625,130 A | | 4/1997 | Grant et al. ................ | 800/306 |
| 5,859,350 A | | 1/1999 | DeBonte et al. ............ | 800/264 |
| 5,866,762 A | | 2/1999 | DeBonte et al. ............ | 800/306 |

OTHER PUBLICATIONS

Kraft et al 2000, Theor. Appl. Genet. 101:323–326.*
Eshed et al 1996, Genetics 143:1807–1817.*
Pechan et al., "Defoliation and Its Effects on Pod and Seed Development in Oil Seed Rape (*Brassica napus* L.)", Journal of Experimental Botany, vol. 36, No. 164, pp. 458–468, Mar. 1985.
Agrawal, P.K. "Effect of Photoperiod on Oil Content, Fatty Acid Composition Protein Content of Rape (*Brassica napus* L.) & Flax (*Linum usitatissimum* L.) Seeds", Indian Journal of Experimental Biology, vol. 9, pp. 252–254, Apr. 1971.
Kumari, N., "The Enfluence of Some Environmental Factors on the Growth, Development and Yield of Rape Seed Mustard", Ph.D. Thesis, Indian Agricultural Research Institute, 1988.
Salisbury et al., "Development Responses in Spring Canola Cultivars", GCIRC Congress, pp. 1769–1774, 1991.
Nuttall et al., "The Effect of Climate on the Yield and Growth of Canola in Western Canada", Project funded by Saskatchewan Agriculture and Food & Saskatchewan Canola Development Commission, pp. 122–127, 1991–1993.
Nuttall et al., "Yield Response of Canola to Nitrogen, Phosphorus, Precipitation, and Temperature", Agronomy Journal, vol. 84, No. 5, pp. 765–767.
Canvin, D., "The Effect of Temperature on the Oil Content and Fatty Acid Composition of the Oils from Several Oil Seed Crops", Canadian Journal of Botany, vol. 43, pp. 63–69, 1965.
Downey, R., K., "The Origin and Description of the Brassica Oilseed Crops", High and Low Erucic Acid Rapeseed Oils, pp. 1–20, 1983.
Fenwick et al., "Glucosinolates and Their Breakdown Products in Food and Food Plants", CRC Critical Reviews in Food Science and Nutrition, vol. 18, Issue 2, pp. 123–201, 1983.

* cited by examiner

*Primary Examiner*—Amy J. Nelson
*Assistant Examiner*—David H Kruse
(74) *Attorney, Agent, or Firm*—Birch, Stewart, Kolasch & Birch, LLP

(57) ABSTRACT

The invention relates to a *Brassica napus* producing a seed designated as NUDB-38 and deposited in the International depository at accession no. PTA-4645, and derived by mutation, which is capable of growing in sub-tropical regions with maturity between about 114 and 141 days after sowing and possessing canola characteristics.

6 Claims, 3 Drawing Sheets

NUDB-38

(2000 X)

Figure 1A:
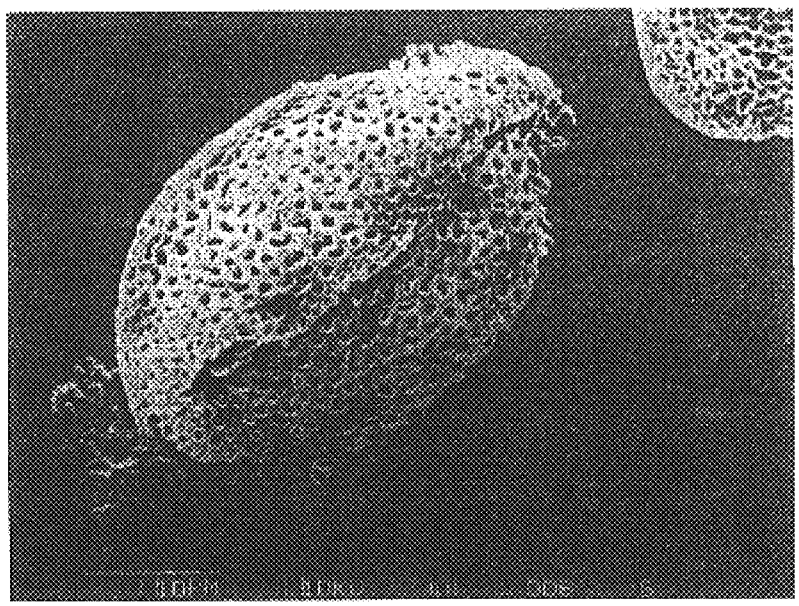

Apocolpium smaller. Coarse reticulation Lumina small brochii irregularly shaped

NUDB-38

(10000 X)

Coarsely reticulate exine, brochii irregularly shaped, muroid ridges thick and uneven margin with smaller lumina.

SEM OF SEEDS

NUDB-38

(200 X)

Reticulation of two types; primary showing hexagonal areas and secondary showing small pits with their ridges marked with striations. Pits circular in shape.

SEM OF SEEDS

NUDB-38

(2500 X)

No. of striations are less. Pits rounded & shallow

SEM OF STIGMA

NUDB-38

(150 X)

Stigma Surface

SEM OF STIGMA

NUDB-38

(1500 X)

Stigma Surface

BRASSICA NAPUS PLANT LINE NUDB-38

This application is a Continuation of U.S. patent application Ser. No. 09/448,294 filed Nov. 24, 1999, now abandoned.

FIELD

The invention relates to a rapeseed (*Brassica napus* L.) line, plant, progeny and seed of the said line. Specifically, the invention relates to a mutant rapeseed line exhibiting canola type characteristics and adapted to grow in subtropical regions, such as India and China. The seeds of the invented line exhibit 'Canola' type characteristics when grown in the said region.

BACKGROUND

To increase the consumption of the rapeseed oil and utilization of the meal left after extraction of oil, plant breeders have focussed their efforts in developing varieties of rapeseed having low erucic acid in the oil and reduced glucosinolate content in the meal remaining after oil extraction. (i.e. erucic acid less than 2% by weight in the oil and glucosinolate content of less than 30 micromoles per gram of deffated meal).

Such lines of rapeseed developed commonly in Canada and Europe are termed as "Canola" or "double low" lines. Examples of such rapeseed lines can be found in U.S. Pat. No. 5,625,130 and U.S. Pat. No. 5,866,762. The plants provided by these patents have been developed through mutagenesis.

PRIOR ART

U.S. Pat. No. 5,387,758 issued to Wong et al relates to improved rapeseed plants, seeds, and improved endogenous vegetable oil having unusually low saturated fatty acid content. Further, the plant possesses herbicide tolerance. The total saturated fatty acid content in the oil yielded by the seeds of these plants is in the range of 2–4% by weight and the erucic acid is not more than 2% by weight based on the total fatty acid content. The plants are obtained by mutagenesis.

U.S. Pat. No. 5,767,338 provides *Brassica napus* plants which produce non-hydrogenated canola oil for food applications. The oil contains 74–80% oleic acid having oxidative stability from 35–40 AOM. This plant again has been grown and tested in various regions in Canada.

U.S. Pat. No. 5,859,350 provides a canola variety producing a seed which yield oil containing less than or equal to 7% linolenic acid and a total glucosinolate content of less than 18 $\mu$.mol/g of defatted meal. U.S. Pat. No. 5,866,762 provides Brassica seed having maximum glucosinolate content of 3.4 $\mu$.mol/g of seed.

All the patents described above relate to plants, their progenies and seeds which have been improved with respect to their oil quality or provide improved meal. The research or study leading to the development of plants in all the aforegoing patents has been done in Canada or its neighbouring countries. In other words, the plants developed according to the aforegoing patents are capable of being grown in Canada or its neighbouring countries, with a cold or cool climate, but not in countries situated in warmer regions such as India. Attempts to introduce the above or similar exotic canola type plants in India have failed due to substantial differences in the climatic conditions between India and the other canola growing regions.

It is pertinent to note that the climatic conditions in India during winter, when the crop is raised, are completely different as compared to the conditions prevailing in Canada in summer, when main crop of canola is grown as shown in Table 1 (a &b) and Table 2 (a &b) below.

TABLE 1a

Maximum and Minimum temperature at various locations in India during rapeseed growing period.

| | R.S. Pura 32.43 N 74.54 E | | Bhatinda 30.11 N 75.00 E | | New Delhi 28.38 N 77.12 E | |
|---|---|---|---|---|---|---|
| Month | Max. | Min. | Max. | Min. | Max. | Min. |
| October | 28.4 | 15.1 | 28.9 | 19.6 | 33 | 14 |
| November | 25.9 | 9.1 | 25.5 | 11.6 | 28.4 | 6.8 |
| December | 18.1 | 4.1 | 17.05 | 9 | 23.2 | 3.8 |
| January | 16.4 | 3.3 | 16.5 | 7.4 | 23.2 | 1.5 |
| February | 20.2 | 5.7 | 21.4 | 9.5 | 27.2 | 3.8 |
| March | 23.7 | 9.1 | 26.85 | 13.05 | 31.6 | 7.8 |

| | Faizabad 26.47 N 82.12 E | | Navagam 26.55 N 70.57 E | | SG Nagar 29.49 N 73.5 E | |
|---|---|---|---|---|---|---|
| Month | Max. | Min. | Max. | Min. | Max. | Min. |
| October | 30.2 | 15.7 | 32 | 19.8 | 31.5 | 16.6 |
| November | 27.5 | 11.1 | 30 | 14 | 28.2 | 10.1 |
| December | 22.1 | 7.4 | 28.7 | 12.1 | 21.2 | 5.9 |
| January | 19.8 | 5.8 | 29 | 12.4 | 19.4 | 4.8 |
| February | 24.6 | 8.5 | 30.8 | 10.7 | 24.8 | 8.8 |
| March | 29.8 | 12.1 | 36.1 | 16.8 | 29.1 | 12.6 |

| | Morena 26.35 N 78.46 E | | SK Nagar 24.12 N 72.28 E | | Agra 27.10 N 78.05 E | |
|---|---|---|---|---|---|---|
| Month | Max. | Min. | Max. | Min. | Max. | Min. |
| October | 31.7 | 19.7 | 32.7 | 20.6 | 31.2 | 19.5 |
| November | 28.8 | 12.65 | 31.2 | 14.9 | 27.3 | 11.4 |
| December | 23.9 | 5.35 | 23.9 | 9.85 | 20.9 | 6.2 |
| January | 20.6 | 4.45 | 26.4 | 8.5 | 19.7 | 5.3 |
| February | 25.25 | 7.45 | 28.6 | 12.5 | 21.6 | 8.4 |
| March | 30.2 | 12.7 | 33.6 | 16.3 | 30 | 12.6 |

| | Kanpur 26.28 N 80.24 E | | Nagpur 21 N, 79.09 E | | Pantnagar 29.40 N 79.33 E | |
|---|---|---|---|---|---|---|
| Month | Max. | Min. | Max. | Min. | Max. | Min. |
| October | 31.2 | 20 | 32 | 21.1 | 30.2 | 19.77 |
| November | 29.6 | 13.8 | 29.55 | 15.8 | 27.73 | 14.06 |
| December | 21.1 | 8.9 | 27.95 | 9.8 | 22.7 | 9.13 |
| January | 20.2 | 6.7 | 28.2 | 10.45 | 20.97 | 7.6 |
| February | 25.7 | 10.9 | 30.95 | 11.3 | 24.9 | 10.06 |
| March | 30.9 | 18 | 37.95 | 17.05 | 29.03 | 14.03 |

TABLE 1b

Average sunshine hours at various locations in India during rapeseed growing period.

| Month | New Delhi | Agra | Faizabad | SG Nagar | Morena | SK Nagaar | Nagpur | Pantnagar |
|---|---|---|---|---|---|---|---|---|
| October | 6.7 | 7.8 | 7.3 | 6.9 | 6.2 | 8.1 | 7 | 7.37 |
| November | 5.5 | 7.7 | 7.7 | 7.9 | 8.2 | 8 | 7.8 | 7.9 |
| December | 4.6 | 5.7 | 5.7 | 5.1 | 7.5 | 8.2 | 9.1 | 6.7 |
| January | 4.6 | 6.4 | 5.9 | 5.1 | 7 | 9.2 | 9.1 | 6.2 |
| February | 7.2 | 8.3 | 8 | 7.4 | 5.3 | 9.1 | 8.7 | 8.3 |
| March | 5.6 | 8.5 | 8.5 | 7.3 | 7.7 | 9.1 | 10.2 | 8.5 |

TABLE 2a

Typical Temperature Variations in Western Canada

| MONTH | MAX. | MIN. |
|---|---|---|
| MAY | 20 | 8 |
| JUNE | 25 | 12 |
| JULY | 30 | 15 |
| AUG | 35 | 10 |
| SEP | 25 | 8 |

TABLE 2b

Sunshine hours in Saskatchewan (as difference between sunset and sunrise)

| MONTH | ESTEVAN | REGINA | SASKATOON | LA RANGE |
|---|---|---|---|---|
| MAY 1 | 15 | 15 | 15 | 15 |
| JUNE 21 | 16 | 17 | 17 | 17 |
| JULY 1 | 15 | 15 | 15 | 16 |
| AUG. 21 | 12 | 12 | 12 | 12 |

The rapeseed crop in India is sown in the month of October when the temperature is suitable for germination and the crop is harvested at the end of winter, i.e. in March–April.

When Canadian Canola type varieties cultivated in India under the above conditions, it is observed that the plant continues to flower till late in the season. In February, the temperature starts rising and reaches around 40° C. by end of March. This forces the crop to attain maturity. It is contemplated that rise in temperature, after flowering could be responsible for poor seed setting. Consequently, increased incidence of flower abortions, poor seed setting, seed size & seed yield etc. are observed in these varieties. Relationship between the curtailed pod length growth at high temperature and also abortion has been explained by Pechan P. A. and Morgan D. G. [J. of Experimental Botany 36:458–468, 1985].

It has emerged that the acclimatization of exotic B.napus L. lines like canola to traditional mustard growing areas in India has almost no scope for commercial exploitation. Agarwal, P. K. [Indian J. Experimental Biology, 9: 252–254, 1971].

Breeding Challenges

Developing widely adaptable canola quality rapeseed for commercial cultivation in the Indian sub-continent is a challenging task.

The rapeseed varieties released in India grow only northern/north-western regions of the country where cool climate is available for production of commercially acceptable seed yield. These lines, however, do not possess the Canola quality characteristics which are desirable from quality point of view.

Thus, there is a need to develop canola-type rapeseed lines that are suitable for commercial cultivation in sub-tropical regions like India with seed yield comparable to that of native Indian rapeseed-mustard varieties and also reatin their canola type characteristics.

Objects

The main object of the invention is to provide mutant seeds of Brassica napus that exhibit canola type characteristics and are suitable for commercial cultivation in sub-tropical regions.

Another object is to provide mutant seeds of Brassica napus that exhibit canola characteristics and mature within 150 days after sowing (DAS) under sub-tropical conditions.

Yet another object is to provide mutant seeds of Brassica napus seed that yield oil whose erucic acid content when grown in sub-tropical regions does not exceed 2%.

Still another object is to provide mutant seeds of Brassica napus wherein seed contains 9.4 micromoles of glucosinolate per gram of seed which is almost equivalent to 17 micromoles of glucosinolate per gram of defatted meal.

Further object is to provide mutant lines of Brassica napus having stable morphological and agronomic characteristics.

Yet another object is to provide mutant lines of Brassica napus seed yielding vegetable oil having improved distribution of fatty acids.

Another object is to provide mutant lines of Brassica napus and producing seed that contains low levels of erucic acid.

These and other objects of the invention will be apparent to those skilled in the art from a reading of the following description and the appended claims.

SUMMARY OF THE INVENTION

The invention relates to mutant seeds of (Brassica napus L.) plants and progenies, which have been adapted to grow in sub-tropical regions. The mutant seeds of the invention have been designated as NUDB-38. The mutant seeds of the invention yield rapeseed oil containing low level of erucic acid. The defatted meal also contains low levels of glucosinolates, when grown in sub-tropical regions. Further, the plants of the invented lines mature within 150 days after sowing. The seed yield of the plants of the invention is better than the native Indian rapeseed Brassica napus L.

DETAILED DESCRIPTION

The present invention relates to mutant seeds of Brassica napus designated as NUDB-38, these seeds produce plants that have been acclimatized to growing in sub-tropical regions where rapeseed and the Indian mustard is commonly grown. The oil from these mutant seeds of NUDB-38 contain less than 2% erucic acid. The defatted meal of the seeds contains less than 17 micromoles of glucosinolates per gram of defatted meal. The plants of the invented line complete 50 percent flowering between 48–60 days after sowing and seed matures within about 114–141 days (Table 3). The seed yield of the mutant plant is also comparable to that of native mustard which is grown extensively in the region.

TABLE 3

Days to 50 percent flowering and maturity.

| Place | Latitude & Longitude | Day Length (hrs) | Days to 50% flowering | Days to seed maturity |
|---|---|---|---|---|
| Nagpur | 21 N, 79.09 E | 7.0–10.2 | 50–54 | 114–118 |
| Raebareli | 26.14 N 81.16 E | 5.7–8.5 | 55–59 | 135–140 |
| Gwalior | 26.14 N 78.10 E | 5.3–8.2 | 52–56 | 134–141 |
| Chandigarh | 30.42 N 76.34 E | 6.6–8.9 | 55–60 | 137–141 |
| Delhi | 28.38 N 77.12 E | 6.6–7.2 | 53–58 | 134–140 |
| Anand | 22.32 N 73 E | 7.5–9.0 | 48–52 | 114–116 |
| Bharatpur | 27.15 N 77.30 E | 5.7–8.5 | 56–58 | 130–134 |
| Mehsana | 23.42 N 72.37 E | 8.1–9.2 | 50–54 | 120–124 |

As used herein, the term "acclimatized" would mean adapted to growing in Indian environment, especially in the regions where rapeseed is grown in India.

"Canola characteristics" refers to the rapeseed plants of Brassica genus which produce seed that contains less than 2 percent erucic acid by weight in its oil and contains less than 30 micromoles of total glucosinolate in its defatted meal.

Mustard refers to the plants of the cultivated Indian mustard (Brassica juncea L.) varieties.

"Day length" refers to availability of sunshine per day in hours.

"Early flowering" means the commencement of flowering in the invented line earlier than the check and is referred in number of days.

'50% Flowering' refers to the initiation of flowering in 50 percent of the plant population.

"Long-day plant" refers to plants that requires more number of sunshine hours per day to flower.

A "line" in the present invention relates to a group of plants that display little or no genetic variations between the individuals. Such lines have been created in the present invention by several generations of self-pollination and selection from a single plant derived from a mutagenized seed.

"Maturity" refers to stage of a plant when it has produced seed which are fully developed and the plants are ready for harvest.

The terms "cultivar" and "variety" refer to a line used for commercial cultivation.

"Progeny" refers to the plants and seeds of all subsequent generations resulting from a single plant.

"Mustard growing region" refers to the regions in India which cover 90 percent acreage of total rapeseed-mustard area.

"Selfed" refers to self-pollination.

"Sunshine hours" means the time between the sunrise and sunset.

"Short day conditions" refers to climatic conditions with less number of sunshine hours per day.

"Sub-tropical" means a region preferably grown between 21° N. and 30° N. latitude and between 72° E. to 81° E. longitude.

The novelty of the invention resides in developing an unique line of Brassica napus plants having the following distinguishing characteristics:

(i) the plants of the invention unlike their counterparts in Canada or Europe have been adapted to grow in completely different agro-climatic conditions, i.e. the sub-tropical regions.

(ii) the plants grow well and flower with 5–10 hours of day length as opposed to the parent canola line which requires 15 to 17 hrs of day length for its growth and flowering.

(iii) the plants mature within 114–141 days after sowing under sub-tropical conditions as against about 85–104 days taken by the canola varieties in Canada.

(iv) the seed produced from the invented line retains the canola character, yield oil containing less than 2% erucic acid and the meal left after extraction of oil contains less than 30 micromoles of glucosinolates per gram.

The plants of the invention have been developed through chemical mutagenesis. Out of the mutagenised population, one distinct mutant plant was isolated, stabilized and tested in various climatic conditions to ascertain its adaptability. The seeds of the invention designated as NUDB-38 has been identified.

Accordingly, the invention provides mutant Brassica napus line exhibiting the following characteristics:

a) capable of being grown in sub-tropical regions, b) having average seed yield of about 1815 kg/ha (936 to 2863 kg/ha).

c) seed maturing between 114 to 141 days after sowing (DAS), and d) producing seeds having not more than 0.1% erucic acid in oil and average of about 17 micro moles glucosinolates per gram of defatted meal.

e) producing seeds having primary and secondary, reticulation on its surface with shallow and circular pits.

In an embodiment, the plants of Brassica napus line are capable of growing in sub-tropical regions selected from Australia, China, India and USA.

In another embodiment, the seed of the plant as described herein above has been deposited at National Bureau of Plant Genetic Resources (NBPGR), New Delhi and allotted a registration no. INGR 01048. The seeds are also deposited under the Budapest Treaty at International Depository (American Type Culture Collection, USA) and have been allotted Patent Deposit Designation: PTA-4645. The deposited seeds will remain readily available to the public for a term of 30 years and for at least 5 years after the last request. Applicants also warrant the permanence of the deposit viability and ready accessibility thereto by the public if a patent is granted, under conditions which assure (a) that access to the culture will be available during pendency of said patent application to one determined by the Commissioner to be entitled thereto under 37 C.F.R. 1.14 and 35 U.S.C. 122, and (b) that all restrictions on the availability to the public of the above-mentioned culture will be irrevocably removed upon the granting of a patent.

The seed deposit was made under the Budapest Treaty. The sample deposit is viable and will be maintained for a period of at least 30 years from the date of the deposit, or five years after the most recent request for a sample, whichever is longer. If the culture should die or become destroyed during the effective term, it will be replaced. The strain will be made available if a U.S. Patent is issued citing the strain or if the U.S. Patent and Trademark Office so instructs the release of the strain.

The invention makes possible the commercial production of canola quality, high yielding rapeseed (Brassica napus L.) in the traditional mustard growing areas in India or in other similar agro-climatic conditions elsewhere.

The invention is further illustrated with reference to the accompanying drawings, examples and description. These illustrations can be practically used, by a person trained in plant breeding art, in developing novel rapeseed line.

BRIEF DESCRIPTION OF THE ACCOMPANYING DRAWINGS

FIGS. 1(a) & (b)—SEM of pollen of the invented plant NUDB-38.

Figure 2A:
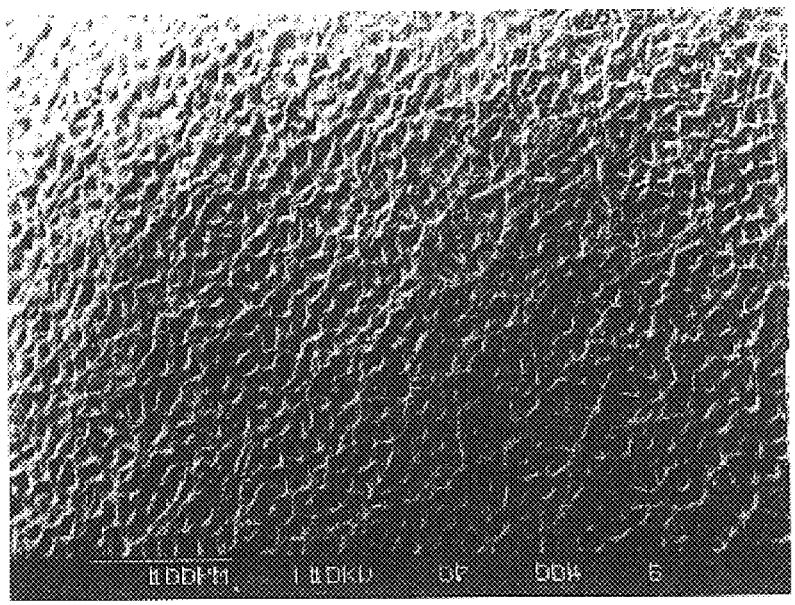

FIGS. 2(a) & (b)—SEM of seeds of the invented plant NUDB-38.

Figure 3A:
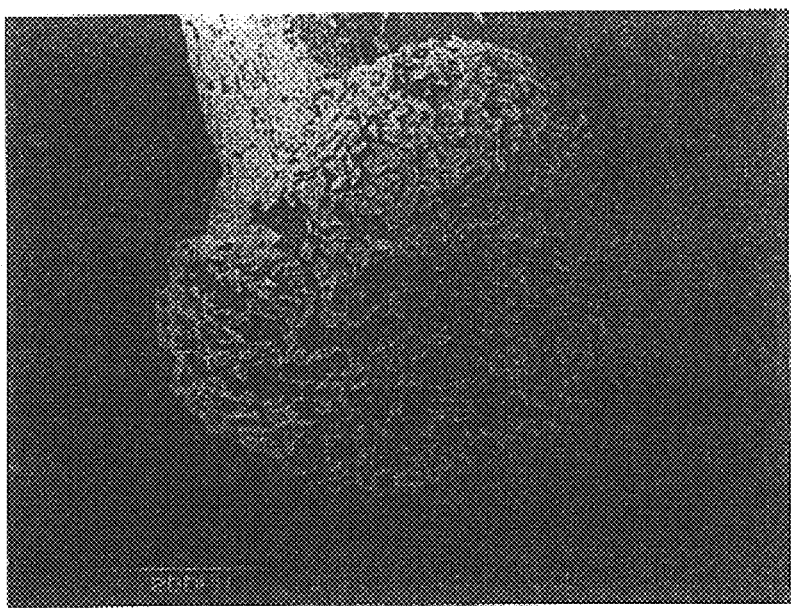

FIGS. 3(a) & (b)—SEM of stigma surface of the flowers of the plant NUDB-38.

Source

Any Canola line can be used as suitable parent for mutagenesis such as some of the semidwarf varieties grown in Canada. The preferred plant would be plants having low glucosinolate level in the meal and low level of erucic acid in the oil such as Westar, Excel, Garrison, Quantum etc. In the present invention, the canola variety 'Westar' was used as the parent. The seeds of westar can be obtained from the seed section, Experimental Farm, Agriculture Canada Research Station, Saskatoon, Saskatchewan, Canada S7N OX2.Westar summer rape (Brassica napus L.) is a canola variety having low erucic acid (0.2%) and low glucosinolate (15 micromoles per gram of defatted meal) content. It has been developed by Klassen A. J, R. K Downey and Capcara, J. J. (Wester Summer Rape; Canadian J Plant Sci., 67: 491–493, 1987). The seeds of 'Westar' were initially multiplied by selfing at Nagpur and genetically pure seeds were utilised for mutagenesis.

Comparison of Temperature/Sunshine Under Typical Ecological Conditions in India and Canada The flowering of Westar is generally controlled by day length and temperature. A long day plant will not produce an economic yield under short day conditions. As presented in table 4, the parent line 'Westar' cannot be grown economically in many parts of the world including India. Table 2b depicts an example of sunshine hours available between sunrise and sunset in Sasketchewan Province in the West Canada. Table 2a depicts typical temperature variations in Western Canada.

Westar matures in about 93–107 days in Canada (Wester Summer Rape; Canadian J Plant Sci., 67: 491–493, 1987). And, this plant when grown in India, takes about 153–169 days to attain maturity(Table 3). The seed yield varies between 1750 to 2350 kg/ha in Canada Canada (Wester Summer Rape; Canadian J Plant Sci., 67: 491–493, 1987) while in India it is about 76 kg to 1050 kg/ha Table 3). The oil content of field grown Westar in Canada varies between 42.4 to 44.2% while when grown in India, it ranges between 38.2 to 41.8%. The oil extracted contains less than 0.2% erucic acid and its defatted meal contains about 15 micromoles of glucosinolate when grown in Canada.

The Applicant studied the growth and development of canola lines in Canada as well as in India and found the variations shown by canola when grown in India are probably on account of the differences in the agro-climatic conditions in the two countries.

TABLE 4

Performance of exotic Brassica napus lines in India (1990–91) along with Brassica juncea

| Variety | Maturity (in days) | | | | | Yield kg/ha | | | | |
|---|---|---|---|---|---|---|---|---|---|---|
| | NVGM | SKN | HSR | PNTR | Mean | NVGM | SKN | HSR | PNTR | Mean |
| Regent | 155 | 163 | 155 | 162 | −159 | 49 | 64 | 1161 | 676 | 488 |
| Westar | 153 | 169 | 153 | 158 | 158 | 76 | 140 | 1050 | 796 | 516 |
| Comet | 154 | 169 | 155 | 167 | 161 | 27 | 222 | 821 | 324 | 349 |
| Consul | 155 | 161 | 156 | 170 | 161 | 53 | 75 | 599 | 704 | 371 |
| WW1507 | 152 | 164 | 141 | 152 | 152 | 333 | 503 | 1517 | 824 | 794 |

NVGM—Navagam (Rajasthan), SKN—Sardar Krushinagar (Gujarat) HSR—Hissar(Haryana), PNTR—Pantnagar (U.P)
Note: all the places indicated in the Table are situated in India Breeding Rapeseed Line (a) Mutagenesis The rapeseed lines may be produced by using induced mutation. Mutagenesis may be accomplished by contacting the plant cells with mutagens selected from physical mutagens viz. X-rays, gamma radiations, neutron, alpha and beta particles or chemical mutagens such as Ethylmethane sulphonate (EMS), ethylene imine (EI), nitrosoethyl urea, nitrosoethyl urethane, N-methyl-N-nitro-N-nitrosoguanidine, sodium azide, or a combination of the above.

In the present invention, the applicant has used sodium azide as the mutagen.

The plant cells of Westar selected from various stages of development like cell culture, embryos, microspores, seeds, pollen, vegetative and shoot parts may be subjected to mutagenesis. The mutation, once achieved, can be transferred to subsequent generations/progenies and/or other species of the plants by cross breeding.

(b) Development of M1 to M9 Generations

About 1350 pure seeds were mutagenized with sodium acide of these different concentrations 0.04, 0.06 and 0.08%. After mutagenesis, the treated seeds were field grown for raising M1 generation. The M1 plants were selfed and M2 seeds harvested individually. The M2 seeds were used to raise M2 generation. The plants that matured within 110–146 days were selected and advanced to M3 generation. The plants of the M3 generation were again screened for early flowering and seed maturity (Table 5). Early flowering and maturing plants were selfed and advanced to the M4 generation on plant to row progeny basis. The plants of the M4 generation were once again screened for early flowering, seed maturity and selfed. The seeds were analyzed for their oil quality. Meal analysis was also done. The plants that flowered within 47–51 days and matured (seed maturity) within 107–113 days and exhibited canola characteristics were carried forward to M5 generation. (Table 6)

TABLE 5

Morphological characters of early mutants in M3 generation.

| M2 Mutant Number | Days to Flower | Plant height (cm) | Siliqua number Per plant | Seed yield/ plant (gm) | Days to Maturity |
|---|---|---|---|---|---|
| Wester | 75 ± 5 | 136.35 ± 2.00 | 61.45 ± 5.97 | 3.76 ± 0.36 | 169 ± 7 |
| 13 | 66 ± 3 | 125.36 ± 2.11 | 69.72 ± 8.52 | 3.63 ± 1.36 | 146 ± 5 |
| 14 | 64 ± 3 | 133.33 ± 2.31 | 80.55 ± 10.38 | 3.65 ± 0.35 | 142 ± 4 |
| 17 | 60 ± 3 | 123.1 ± 2.30 | 54.7 ± 4.00 | 4.45 ± 0.34 | 141 ± 5 |
| 19 | 63 ± 4 | 131.46 ± 4.43 | 108.73 ± 6.89 | 3.70 ± 0.34 | 145 ± 5 |
| *20 | 45 ± 7 | 108.5 ± 3.14 | 113.4 ± 15.8 | 5.6 ± 0.9 | 110 ± 6 |
| 22 | 60 ± 3 | 130.35 ± 1.82 | 66.14 ± 7.78 | 4.26 ± 0.38 | 141 ± 5 |
| 24 | 64 ± 5 | 145.73 ± 0.86 | 70.86 ± 7.44 | 5.92 ± 0.72 | 146 ± 5 |

TABLE 6

Morphological Characters of M-4 selections.

| Selection | Plant height cm | Days to Flower | Seed yield/plant | 1000 seed wt.(g) | Oil % | Days to Mature |
|---|---|---|---|---|---|---|
| Westar | 129.0 ± 2.2 | 75 ± 3 | 3.8 ± 1.5 | 4.2 ± 0.22 | 40 ± 1.8 | 164 ± 5 |
| Sel-38 | 109.62 ± 2.18 | 49 ± 2 | 12.55 ± 2.0 | 4.2 ± 0.39 | 40.22 ± 1.3 | 110 ± 3 |

The criteria for selection of plants always remained early seed maturity with canola type oil characteristics. Yield trials were carried out with M6 to M9 generation (Table 7). Multi-location trials were carried out during M9 for studying the adaptability to different regions and assessment of suitability for commercial cultivation. These plants have exhibited higher yield potential as compared to native *Brassica napus* variety HPN-3 and were comparable with native Indian mustard varieties such as Pusa Bold and Varuna (Table 8).

TABLE 7

Comparative Seed yield of NUDB-38 at Nagpur from M6 to M9

|  | M6 | M7 | M8 | M9 | Mean |
|---|---|---|---|---|---|
| Seed Yield (kg/ha) | | | | | |
| NUDB-38 | 803 | 984 | 936 | 935 | 915 |
| Varuna | 838 | 960 | 908 | 715 | 855 |
| HPN-3 | 316 | 515 | 365 | 465 | 415 |
| Maturity (in Days) | | | | | |
| NUDB-38 | 109 | 116 | 107 | 112 | 111 |
| Varuna | 110 | 112 | 110 | 116 | 112 |
| HPN-3 | 126 | 130 | 124 | 132 | 128 |

The invented line NUDB-38 was a selection from M3 generation and stabilized over M4 to M9 successive generations.

The plants of the invented line complete 50% flowering between 48 to 60 days and mature between 114 to 141 days when planted within narrow band of specified sowing time in the month of October/November The lines of the invention have been grown and tested in different regions in India viz. Nagpur (Maharashtra), Mehsana and Anand (Gujarat), Delhi, Chandigarh (Punjab), Bharatpur (Rajasthan), Raebareli (U.P.) and Gwalior (Madhya Pradesh). Though the critical day lengths in these places were different, the plants of the invented line exhibited substantially similar flowering period (Table 3).

The rapeseed line of the invention are substantially genetically homozygous and thus can be reproduced by self pollination. The invented line show phenotypic uniformity and stability within limits for all traits described herein.

Under standard Indian production practices, the rapeseed plants of the invented line produce an average dried seed yield between 936 to 2863 kg/ha which is comparable to seed yield of Pusa Bold (1032 to 3304 kg/ha) and Varuna (908 to 3305 kg/ha) under similar conditions. Rapeseed line of the invention is white rust disease resistant like its parent 'Wester'.

TABLE 8

Comparison of seed yield (kg/ha) of NUDB-38 with other popular lines

| Line | Salon | Mehsana | Nagpur | B'pur-I | B'pur-II | Ch'garh | Anand | Gwalior | Dehli | Average |
|---|---|---|---|---|---|---|---|---|---|---|
| Varuna | 1067 | 2132 | 908 | 1616 | 1942 | 1164 | 3246 | 3305 | 2082 | 1940 |
| Pusa Bold | 1032 | 1662 | 1080 | 1122 | 2079 | 1235 | 3304 | 3051 | 1980 | 1838 |
| HPN-3 | 680 | 555 | 515 | 755 | 1887 | 1649 | 1894 | 1960 | 1976 | 1319 |
| NUDB-38 | 1765 | 1760 | 936 | 1212 | 1904 | 1892 | 2209 | 2863 | 1797 | 1815 |

Varuna and Pusa Bold—*Brassica juncea*
HPN-3—*Brassica napus*

Morphological Characteristics

The average test weight of NUDB-38 seed is around 3.2 to 4.3 g. The seed size is greatly influenced by the environmental factors. However, under normal conditions the seed size of the invented lines was found to be smaller than the seed size of the popular Indian mustard varieties which have test weight between 4 to 5 g.

Rapeseed of the Invention

The oil content in seed is greatly influenced by agro-climatic factors, more particularly the temperature at the time of seed filling. The average oil, glucosinolate and fatty acid composition in NUDB-38 from M4 to M9 generations is given in Table 9.

TABLE 9

Fatty acid composition of oil produced from seed of NUDB-38

| Generation | Average Oil Content in seed (in %) | Glucosinolate moles/g of seed | Palmitic Acid (16:0) | Stearic Acid (18:0) | Oleic Acid (18:1) | Linoleic Acid (18:2) | Linolenic Acid (18:3) | Erucic Acid (22:1) # |
|---|---|---|---|---|---|---|---|---|
| M4 | 41.36 | 9.10 | 4.23 | 1.86 | 68.07 | 17.47 | 6.97 | 0.00 |
| M5 | 41.83 | 9.57 | 4.35 | 1.67 | 67.55 | 17.43 | 7.02 | 0.00 |
| M6 | 40.51 | 9.20 | 4.30 | 2.13 | 67.19 | 17.30 | 7.04 | 0.00 |
| M7 | 39.61 | 9.44 | 4.85 | 2.07 | 68.46 | 16.33 | 7.06 | 0.00 |
| M8 | 41.33 | 9.81 | 4.11 | 2.26 | 68.22 | 16.13 | 7.66 | 0.00 |
| M9 | 40.86 | 9.33 | 4.25 | 1.98 | 68.08 | 17.11 | 7.48 | 0.00 |

The seeds of the invented lines exhibit fatty acid profile with less than 0.1% erucic acid. Other typical oil characteristics of the invented lines is given in Table 10 which confirms similarity with the canola oil.

TABLE 10

Typical oil characteristics of the invented lines

| Oil Characteristics | NUDB-38 | Canola Oil |
|---|---|---|
| Saponification value | 189–190 | 166–198 |
| Iodine value | 101–102 | 94–126 |
| Bellier's Turbidity Test (° C.) | 17 | Maximum 19 |

TABLE 11

Selection Criteria used in developing NUDB-38

| Generation | Selection Criteria & line isolation | Location (In India) |
|---|---|---|
| M-1 | No selections were made | Nagpur & Leh |
| M-2 | Early Flowering, Early maturity and other morphological | Nagpur |
| M-3 | Study of the Breeding behavior of mutant and selections were made for early flowering and maturity. | Nagpur |
| M-4 | Observations made for characters same as in M 3. Additional parameters on seed yield and plant type were noted. Oil quality parameters were studied. | Nagpur |
| M-5 | Behavioural Confirmation of the characteristics selected lines. Also a station trial to study agronomic characteristics and quality evaluation was made simultaneously and seed increase. | Nagpur |
| M-6–8 | Multi-locational trials for yield evaluation, and seed increase, quality evaluation | Mehsana, Raebareli, Gwaliar, Chandigarh, Bharatpur, Anand, Delhi, Nagpur. |
| M-9 | Multi-locational trials, On-farm trials and seed increase, quality evaluation | Mehsana, Raebareli, Gwaliar, Chandigarh, Bharatpur, Anand, Delhi, Nagpur. |

Testing of Seed Quality Traits

The screening of plants and seed traits for desirable may be done by means of any established method/procedure. The ability to precisely quantify desired seed/oil quality traits in very early and subsequent generations is very vital for the success of the breeding programme. Similarly, the ability to do a complete quality analysis on single plant/seed basis is very critical in finding rare segregants exhibiting an optimum combination of the desirable plant and seed 'quality traits'. Thus preferred screening methods are those that are highly precise and sensitive and require minute amount of sample material. Examples of such preferred methods include use of NMR and soxhlet methods for oil content determination in seed, GLC for fatty acid composition and testape (for screening large populations) and HPLC for glucosinolates determination. The procedures described below are by way of illustrations and not limitations. They may be substituted by known equivalents and procedures:

A: Seed i. Oil Content Determination in Seed a. NMR:

For initial screening of oil content in seed, ISO 5511:1992 Oilseeds—Determination of oil content—method using continuous wave low-resolution Nuclear Magnetic Resonance Spectrometry was used.

b. Soxhlet method:

AOCS Official Method Am2-92 Oil Content in Oilseeds was used to determine the oil content in seeds.

ii. Glucosinolate Content a. Testape method:

The initial screening for identifying the low levels of glucosinolates in the seeds of invented lines was made using Testape method developed by D. I Mc Gregor and R. K. Downey, 1975 (A Rapid and Simple Assay for Identifying Low Glucosinolate Rapeseed, Can. J. Plant Science, 66:191–196, 1975).

Following steps were involved in the method:

i. 5 seeds were placed in a well of the microtiter plate.

ii. Seeds were crushed using rod and light hammer stroke iii. About 100 μl of distilled water was added and waited for 10 minutes.

iv. 50 μl Charcoal solution (70 g/l) was added and waited for one minute.

v. Testape strip was placed and after 5 minutes its colour was observed. The colour of testape strip(s) were matched with the chart readings which indicate the amount of glucose either in percent (0 to 2%) or in relative figures (0 to ++++). A colour shade lighter than or equal to that shown as 1/10% glucose (0 and + relative scale), indicated the seed of canola quality. A colour shade at 1/4% level (the +++ and ++++ relative scale) indicated seed is not of canola quality. A colour shade at 1/4% level (the ++ relative scale) indicated the seed is near upper level of glucosinolates for canola quality (i.e. 18 μmoles per gram of seed).

b. HPLC method:

ISO 9167-1 1992(E) Rapeseed-Determination of glucosinolate content—Part -I: Method using High-performance Liquid Chromatography was used for estimation of glucosinolate in the seed.

B. Oil i. Fatty Acid Composition

The fatty acid analysis was carried out by GLC method using AOAC official method Ce 1–66 for preparation of methyl esters of long chain fatty acids and Ce 2–66 for Fatty Acid Composition.

ii. Saponification value (the number of milligrams of potassium hydroxide required to saponify completely one gram of oil).

The saponification value of oil was determined through AOCS Official method no. Cd 3–25 (1989).

iii. Iodine value (The total unsaturated double bonds present in the oil).

The Iodine value was determined by using AOCS Official Method No. Cd 1–25 (1989).

iv. Belleir Turbidity Temperature (temperature at which the long chain fatty acids precipitate when their alcoholic soap solution is treated with diluted acetic acid and ethyl alcohol).

One ml of the filtered sample oil was taken in a flat bottom 100 ml conical flask, 5 ml of 1.5N alcoholic potassium hydroxide was added and saponified completely by heating over a boiling waterbath using air condenser to avoid loss of alcohol. During saponification flask was swirled several times. After cooling, 0.1 ml of phenolphthalein indicator was added then neutralized by carefully adding dilute acetic acid with an extra amount of 0.4 ml. 50 ml of 70 percent alcohol was added and mixed. A thermometer (0–60° C.)was fitted in the flask. The flask was heated gently over a water bath until temperature reached 50° C. and the solution was clear. The flask is cooled gradually at the rate of 2° C. per minute. The temperature at which the first distinct turbidity appears is noted. The precipitate was dissolved by gently heating to 50° C. and again cooled and turbidity temperature was noted within ±0.5° C.

Example 1

Account of Breeding of NUDB-38

Selfed seed of Westar were pre-soaked in distilled water for a period of 12 hours before treatment. On the completion of soaking, water was drained off and seeds were surface dried on absorbent paper. An aqueous solution of sodium azide (SA) [$NaN_3$, manufactured by E. Merck, Darmstadt, Germany] was prepared in glass double distilled water on w/v basis with three different concentrations viz. 0.04, 0.06 and 0.08%. Soaked seeds were treated in freshly prepared 50 ml of mutagen solution. Total 1350 seeds were mutagenised at 24±0.5° C. with 120 rpm in Remi Orbital Shaker incubator with three concentrations each with three replications. An individual control was also maintained exactly like the treated seeds. After completion of treatments, the seeds were thoroughly washed in running water and post-soaked in distilled water for 1 hour under continuous shaking in orbital shaker.

Out of 150 treated seeds in each replication, 100 seeds were sown directly in the experimental field for raising M 1 generation. The treated seeds were sown in the field with 30 cm row to row distance and about 10 cm plant to plant distance. Although the treated seed showed over 85% germination under lab conditions, only 16% of the plant population reached to maturity under field condition. The $M_1$ plants were selfed and 148 plants were harvested individually.

Approximately 4586 M 2 plants were grown from M 1 plants on plant to row progeny basis in the field at a distance of 45 cm between rows and 15 cm between plants in winter season at Nagpur and screened for morphological mutations. The mutants affecting flowering, maturity, seed yield and other morphological character were identified and selfed.

Seven mutants were selected for early flowering and seed maturity. The flowering duration of these mutants ranged between 55–69 days. These plants were selfed and grown in M 3 generation. 6 mutants bred true for flowering and maturity. The flowering in these mutants ranged between 57–69 days and maturity between 136–151 days as against 162–176 days maturity in Westar (Table 5). They were early as compared to parent but very late in comparison to the Indian mustard varieties. Therefore, they were not found suitable for Indian conditions. The progeny of one of the mutants (No. 20; from 0.06% SA treatment) flowered within 52 days and matured before 116 days. Four plants were selected from this mutant based on early flowering, early maturity and high yield. The true breeding behavior of these lines was confirmed in M4 generation. The additional criteria used was seed yield (above 10 g per plant) and oil content (above 40%). The quality parameters viz. erucic acid and glucosinolate content was also analyzed and found to be closer to parent.

Out of the four the invented line the selection 38 flowered in 50 days attained maturity in 110 days, was identified and carried forward (Table 6).

Selections 38 was advanced to M5 generation for studying the true breeding behaviour. Also for assessing its yield potential, a station trial was conducted alongwith the popular varieties viz. GM-1, Pusa Bold and Varuna.(Table 12). The breeding behaviour for early maturity was again confirmed and the sufficient quantity of seed was produced for undertaking multi-locational trials.

TABLE 12

Comparison of invented line and popular varieties At Nagpur

| Variety | Height (cm) | Flower initiation (days) | 50% Flowering | Maturity (days) | Seed Yield kg/ha |
|---|---|---|---|---|---|
| Pusa Bold | 192 | 45 | 53 | 111 | 1080 |
| Varuna | 171 | 45 | 53 | 112 | 908 |
| HPN-3 | 170 | 52 | 62 | 126 | 515 |
| NUDB-38 | 141 | 45 | 51 | 116 | 892 |

Example 2

Comparative Performance of Rapeseed Under Typical Ecological Conditions in Indian Sub-Continent

*Brassica napus* is grown parts of northern India viz. Jammu & Kashmir, Punjab and Himachal Pradesh. *Brassica napus* varieties do not grow well in regions where temperature is greater than 35° C.–40° C. and where winter is of shorter duration. Efforts made to introduce exotic *Brassica napus* has not been successful because all exotic varieties when grown in traditional mustard grown areas, they continue to grow until December and flower as late as February. In February temperature starts rising and a majority of the flowers do not develop into fully grown pods, often resulting in abortion of pods. The performance of a few exotic varieties at some of the locations in India is given in Table 4.

In order to assess the performance of the invented lines under different agro-ecological conditions, the yield trials were conducted at ten locations for two years to establish stability of the line.

Example 3

Morphological, Agro-Nomical and Chemical Features of the Invented Line.

(a) SEM of Pollen of the Invented Line

Figure 1B:
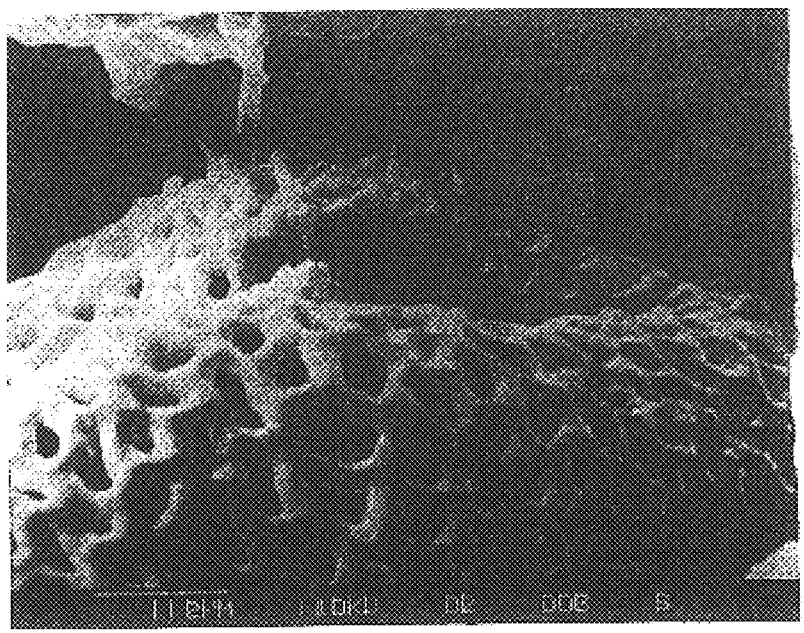

FIG. 1 (*a* & *b*) shows SEM of pollen of NUDB-38 with magnification level of 2500 X and 10000 X and pollen characters viz. apocolpium, Muri, lumina, reticulation and brochi are explained in Table 13.

TABLE 13

SEM observation on Pollen Grains of invented lines of *Brassica napus*

| Characters | NUDB-38 |
|---|---|
| Apocolpium | Broad |
| Muri | Thick without protruberences |
| Lumina | Small |
| Reticulation | Coarse and not Uniform |
| Brochi | Heteroprochate, oval, rectangular or renticular |

(b) SEM of Seeds of the Invented Line

Figure 2B:
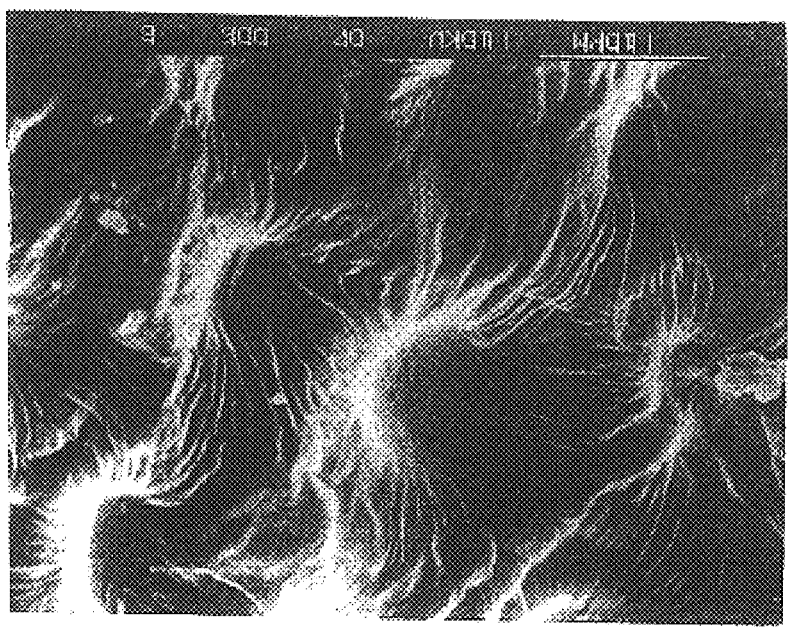

FIG. 2 (*a* & *b*) depicts SEM of NUDB-38 seeds at magnification level of 200 X and 2500 X. Description on seed characters viz. colour, size, surface, reticulation and pits are given table 14.

TABLE 14

Seed Morphology and SEM observation of the invented line of *Brassica napus*

| Characters | NUDB-38 |
|---|---|
| Colour | Black with brownt shade |
| Size | 2.0–2.5 mm |
| Surface | Reticulated with distinct pits |
| Reticulation | Two types of reticulation<br>a) Primary<br>b) Secondary |
| Pits | Shallow and Circular in shape |

(c) SEM of Stigma of the Invented Line

Figure 3B:
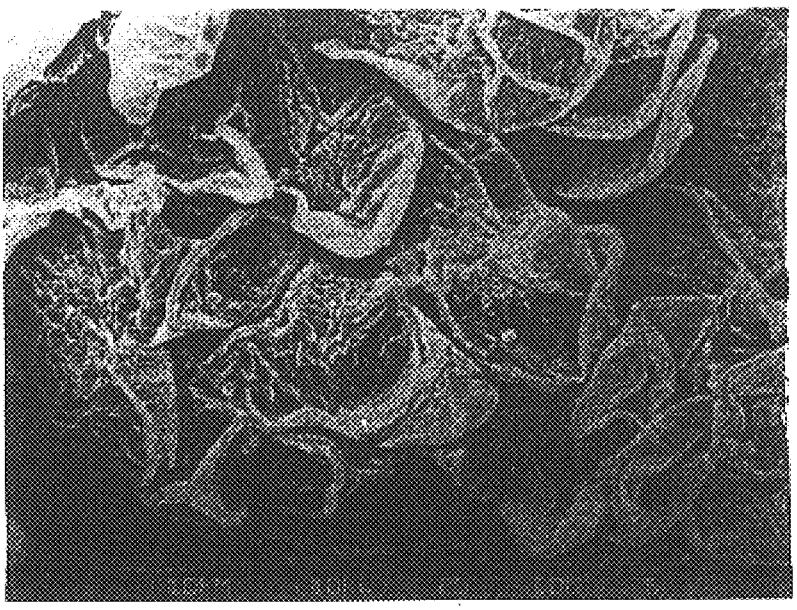

FIG. 3 (*a* & *b*) shows 1500 X SEM of stigma surface of NUDB-38 showing its surface, shape and arrangement (table 15).

TABLE 15

SEM observation of Stigma of the invented lines of *Brassica Napus*

| Characters | NUDB-38 |
|---|---|
| Stigma Surface | Papillate |
| Papilla - Shape | Petaliferous |
| Surface | Heavily reticulated |
| Arrangement | Compact |

Agronomic and Morphological Characteristics

NUDB-38 plants have a spreading habit and are, comparatively shorter than that of the parent line with longer internodes. The older leaves of NUDB-38 were devoid of red pigmentation which was present in the parent line.

Accordingly, the invention provides a novel mutant *Brassica napus* line, which when grown in the sub-tropical regions exhibits the following characteristics:

a. has mature plant height of 129–220 cms, b. capable of being grown in sub-tropical regions having average temperature of about 4° C. to 45° C. and relative humidity of about 20% to 60%, c. maturing between 114 to 141 days, d. producing seeds having not more than 0.1% erucic acid and meal having average of about 10 micro.moles per gram glucosinolates The pollen and stigma of the mutant plant is shown in FIGS. 1 to 3.

Table 8 shows the results of multi-locational yield trials conducted in the states of Gujarat, Maharashtra, Madhya Pradesh, Rajasthan, Uttar Pradesh and Punjab.In multi-locational trials, NUDB-38 showed better yield than conventional varieties. This further confirms that the invented line with better quality characters can be successfully grown in traditional mustard areas. This also confirms the fact that these plants can be grown in all such sub-tropical regions. Such places could be for instance, Australia, China, Canada, and USA.

Plant height and duration for maturity of the invented lines in northern regions was more than the central—western regions.

What is claimed is:

1. A seed of *Brassica napus* designated as NUDB-38 and deposited in the International depository at accession no. PTA-4645, which is capable of growing in sub-tropical regions with maturity between about 114 to 141 days after sowing and possessing canola characteristics.

2. The seed as claimed in claim 1, wherein the seed produces a plant having 50 percent flowering between 48 to 60 days and matures between 114 to 141 days under sub-tropical regions.

3. The seed as claimed in claim 1, wherein said seed contains about 40.8 ±2% oil.

4. The seed as claimed in claim 3, wherein the oil further contains not more than 0.1% erucic acid by weight.

5. The seed as claimed in claim 1, wherein an extraction from said seed obtained after removing oil from said seed contains glucosinolate of not more than 17 micromoles per gram of defatted meal.

6. The seed as claimed in claim 1, wherein said seed is a mutant of Westar.

* * * * *